US009805481B2

(12) United States Patent
Sperl et al.

(10) Patent No.: US 9,805,481 B2
(45) Date of Patent: Oct. 31, 2017

(54) SYSTEM AND METHOD FOR REGULARIZED RECONSTRUCTION OF PHASE CONTRAST COMPUTERIZED TOMOGRAPHY

(71) Applicant: General Electric Company, Schenectady, NY (US)

(72) Inventors: Jonathan Immanuel Sperl, Baveria (DE); Dirk Beque, Bavaria (DE)

(73) Assignee: General Electric Company, Niskayuna, NY (US)

(*) Notice: Subject to any disclaimer, the term of this patent is extended or adjusted under 35 U.S.C. 154(b) by 98 days.

(21) Appl. No.: 15/004,293

(22) Filed: Jan. 22, 2016

(65) Prior Publication Data

US 2017/0213364 A1 Jul. 27, 2017

(51) Int. Cl.
G06K 9/00 (2006.01)
G06T 11/00 (2006.01)
G01N 23/04 (2006.01)

(52) U.S. Cl.
CPC .......... G06T 11/003 (2013.01); G01N 23/046 (2013.01); G01N 2223/401 (2013.01); G06T 2211/40 (2013.01)

(58) Field of Classification Search
CPC ....... A61B 6/032; A61B 6/037; G01T 1/1611; G01T 1/1644; G01T 1/169

(Continued)

(56) References Cited

U.S. PATENT DOCUMENTS 8,326,054 B2* 12/2012 Chen .................. A61B 6/032
378/4
9,600,910 B2* 3/2017 Wang .................. G01T 1/1647
(Continued)

FOREIGN PATENT DOCUMENTS

WO 2013159044 A1 10/2013
WO 2013188957 A1 12/2013

OTHER PUBLICATIONS

Smith David S. et al., "Robustness of Quantitative Compressive Sensing MRI: The Effect of Random Undersampling Patterns on Derived Parameters for DCE- and DSC-MRI", IEEE Transactions on Medical Imaging, vol. 31, No. 2, Feb. 2012 (pp. 504-511, 8 total pages).

(Continued)

Primary Examiner — Charlotte M Baker
(74) Attorney, Agent, or Firm — Pabitra K. Chakrabarti

(57) ABSTRACT

Reconstructing under-sampled PCT data includes obtaining under-sampled scan data of a subject-under-test, the object scan performed on a phase contrast computed tomography (PCT) system, performing a regularized Fourier analysis on the under-sampled scan data, correcting for one or more PCT system contributions to the under-sampled scan data by dividing the computed Fourier coefficients by Fourier coefficients representative of the one or more PCT system contributions, obtaining at least one of an absorption sinogram, a differential phase sinogram, and a dark field sinogram from the corrected Fourier coefficients, and performing tomographic reconstruction on the obtained absorption sinogram, the obtained differential phase sinogram, and the obtained dark field sinogram. A system and non-transitory computer readable medium are also disclosed.

20 Claims, 7 Drawing Sheets

(58) Field of Classification Search
USPC .......................... 382/131, 132, 232; 378/4, 8
See application file for complete search history.

(56) References Cited

U.S. PATENT DOCUMENTS

| | | |
|---|---|---|
| 2010/0207629 A1 | 8/2010 | Trzasko et al. |
| 2011/0058719 A1 | 3/2011 | Trzasko et al. |
| 2012/0092009 A1 | 4/2012 | Zhang et al. |

OTHER PUBLICATIONS

Vasanawala, SS et al., "Practical Parallel Imaging Compressed Sensing MRI: Summary of Two Years of Experience in Accelerating Body MRI of Pediatric Patients", Biomedical Imaging: From Nano to Macro, 2011 IEEE International Symposium on, 2011, (pp. 1039-1043, 5 total pages).

Oh, Heeseok et al., "Visually weighted reconstruction of compressive sensing MRI", Magnetic Resonance Imaging, vol. 32, Issue 3, (2013-2014), Elsevier, (pp. 270-280, 11 total pages).

Jorgensen, Jakob S. et al., "How little data is enough? Phase-diagram analysis of sparsity-regularized X-ray CT", Dec. 23, 2014, (pp. 1-24, 24 total pages).

Roujol, Sebastien et al., "Accelerated free breathing ECG triggered contrast enhanced pulmonary vein magnetic resonance angiography using compressed sensing", Journal of Cardiovascular Magnetic Resonance, vol. 16, No. 91, 2014, 9pgs.

\* cited by examiner

WHERE ω: VIEWS, $X_g$: PHASE STEPS

SYSTEM AND METHOD FOR REGULARIZED RECONSTRUCTION OF PHASE CONTRAST COMPUTERIZED TOMOGRAPHY

BACKGROUND

Systems used for image reconstruction (e.g., computed tomography (CT), phase contrast CT (or PCT), magnetic resonance imaging (MR, or MRI), etc.) can implement (potentially randomized) undersampled data acquisition in combination with compressed sensing image reconstruction to obtain viewable images from the collected scan data. This imaging can be performed for medical, preclinical, industrial, and other purposes. The collection of suitable scan data (i.e., data with a high signal to noise ratio), can expose the scan subject to large doses of radiation (i.e., for CT and PCT imaging). This exposure to radiation gives rise to concerns of increased risk of developing cancer.

Scan techniques can be implemented with lower radiation doses and/or under-sampling of data points to minimize the patient's exposure to radiation. Dedicated image reconstruction techniques are applied to this under-sampled data to generate reconstructed images of comparable image quality to images generated from non-undersampled data. Tomographic reconstruction from a limited number of scan projections can thereby be obtained. Conventional image reconstruction methods are limited to scan data without violation of the Nyquist sampling criteria and/or without the presence of substantial amounts of noise. When these conditions are not met, the accuracy of reconstructions using conventional techniques can be considerably diminished.

PCT data can be considered as four dimensional (4D), namely: phase steps, view angles, and the column/row directions of the detector. The data from the phase stepping direction is unique for PCT and requires Fourier analysis. Other approaches for processing under-sampled data can be based on interpolation of the data (typically prior to image reconstruction, i.e., as a preprocessing step) in combination with a conventional image reconstruction approach. Another approach includes compressed sensing of random under-sampling in the view-domain only for Phase Contrast CT (and not along the phase steps). Under-sampling methods can be used to speed up data acquisition and/or lower the patient x-ray dose exposure, without significant loss of image quality. For example, grating based Phase Contrast CT requires sampling in the four dimensional phase step/ view angle/detector column/detector row direction.

DESCRIPTION

In accordance with embodiments, systems and methods regularize the reconstruction, including the Fourier analysis part, of under-sampled and/or low-dose (noisy) imaging data (instead of simple interpolation) to improve the image quality based on prior knowledge. In some implementations, random under-sampling schemes can be utilized to improve the results according to the concept of compressed sensing. Embodying systems and methods regularize the Fourier analysis of the phase stepping dimension data from PCT acquisitions. Embodying systems and methods support (random) subsampling in the phase step direction as well as low-dose (noisy) measurements.

Conventional approaches for data reconstruction utilize interpolation to fill sampling space. Such conventional approaches result in a loss of resolution. Embodying systems and methods combine phase contrast CT with compressed sensing reconstruction while exploiting prior knowledge. The exploitation of prior knowledge enables higher under-sampling factors, yielding a higher reduction in scan time and lower patient radiation exposure.

Faster image data acquisition resulting from reduced scan time can expand the applicability of PCT imaging. For example, intraoperative pathology and phase contrast mammography-CT are two medical applications that can benefit from embodying systems and methods. For preclinical imaging, the anesthesia duration of the scan subject can be reduced. New industrial applications can include non-destructive testing.

Figure 1:
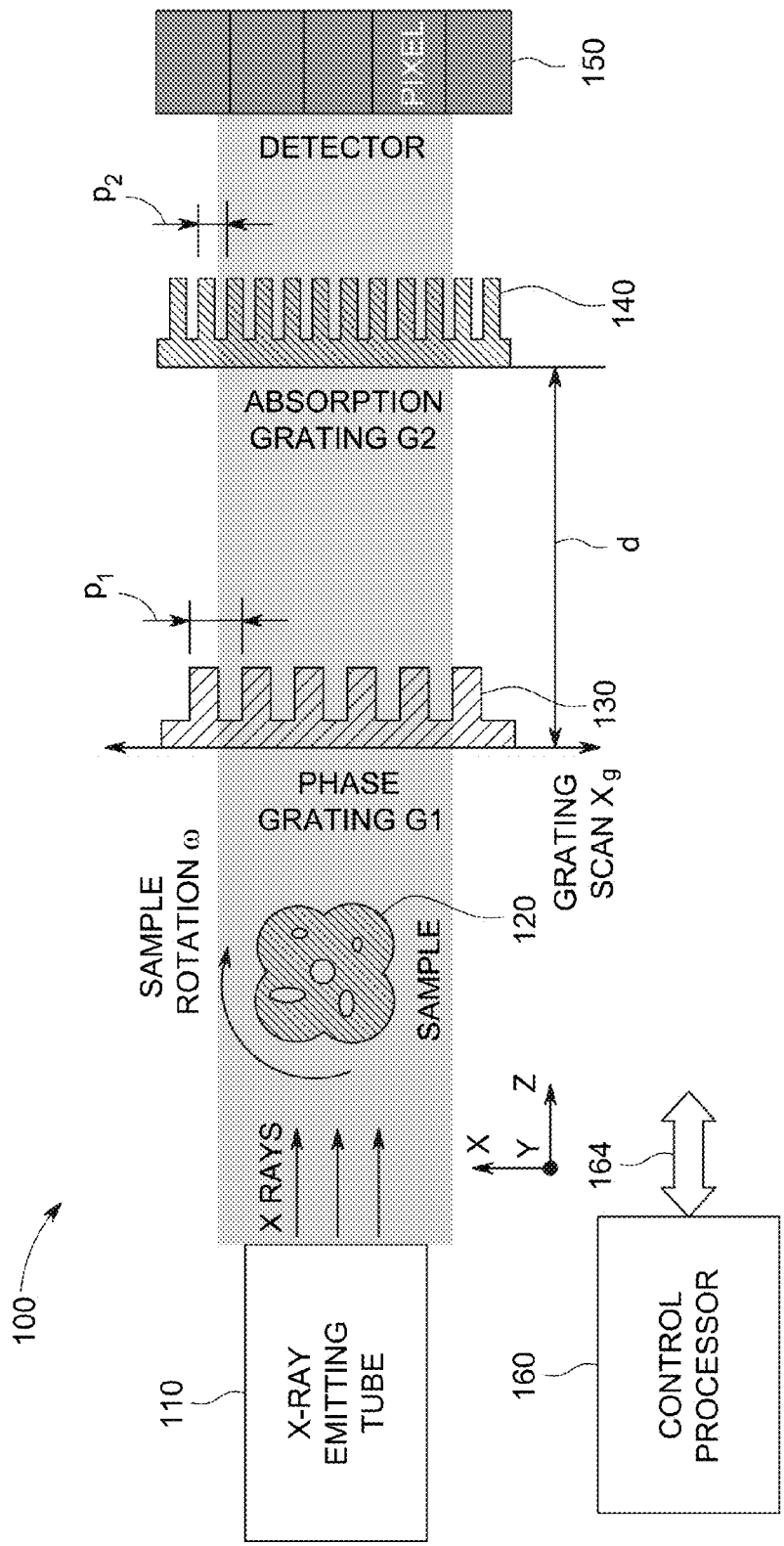
FIG. 1 depicts a conventional phase contrast CT scan system.

FIG. 1 depicts a conventional grating-based phase contrast CT scan system 100. System 100 includes x-ray emitting tube 110 that emits x-rays towards scan subject 120. The scan subject can be rotated over the angle co to expose the subject to x-ray radiation from different angles for the purpose of data acquisition. Alternatively, the subject can remain stationary and the emitting tube can be moved with respect to the scan subject—for example, by being mounted on a rotating gantry.

After partial absorption, refraction and scattering (giving rise to the absorption, phase and dark field part of the signal respectively) by the scan subject, the attenuated x-ray beam is incident on phase/absorption grating window 130. The phase/absorption grating window has a grating spacing $p_1$. The grating window 130 induces interference effects in the x-ray beam transmitted through it. Absorption grating window 140 (with a grating spacing $p_2$) is set a predetermined distance d from phase/absorption grating window 130. The absorption grating selectively blocks part of its incident x-ray beam interference pattern. The remaining part of the incident x-ray beam reaches x-ray detector 150. Detector 150, which includes multiple pixels, senses the impinging x-rays and provides pixel signals proportionate to the sensed event.

In-plane motion of absorption grating 140 by small increments of grating period $p2$, called phase stepping, exposes each detector pixel to different parts of the x-ray interference pattern, yielding a detector signal that is periodic as a function of the position of grating 140 with period $p2$.

The CT scan system includes control processor 160 which executes computer readable instructions to control the operation of system 100. The control processor communicates with the components of system 100 via bus 164. It should readily be understood that other system configurations and/or operation modes are equally possible. Some systems have, for example, an additional absorption grating between x-ray source 110 and the scan subject. Some systems can move phase/absorption grating 130 instead of absorption grating 140 to perform phase stepping.

Figure 2A:
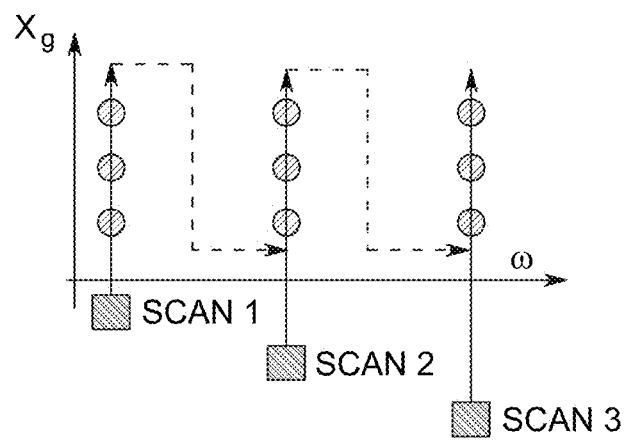
FIGS. 2A-2D depict conventional phase contrast CT sampling schemes.

FIGS. 2A-2D depict conventional two dimensional sampling schemes for phase contrast CT scans, where the horizontal axis (ω) represents the view angle and the vertical axis (Xg) represents the phase stepping. The column and row detector directions are not shown and assumed to be completely sampled. FIG. 2A depicts a conventional fully sampled scan, where a complete series of phase steps is acquired for every particular view. This requires a step-and-shoot type of acquisition—i.e., without continuous scan subject rotation.

Figure 2B:
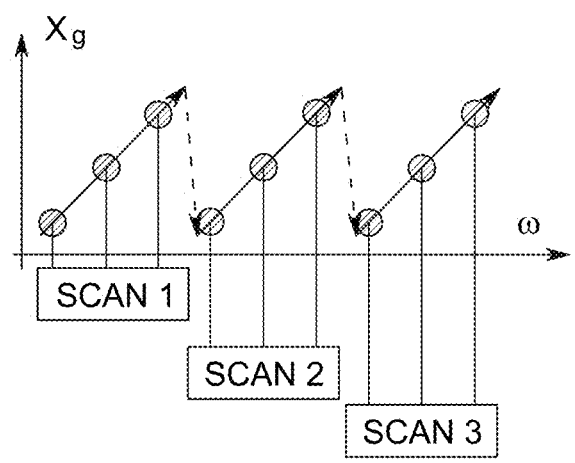

FIG. 2B depicts a conventional scan pattern with simultaneous phase step and view angle motion of the acquisition system, which is more compatible with continuous rotation of the scan subject than the scan pattern of FIG. 2A. For conventional image reconstruction the phase steps from three consecutive view angles are treated as if they were acquired at a single view angle, which can be considered a kind of nearest neighbor interpolation. This scheme can cause blurring in the reconstructed images, but seems to help reduce artifacts in local tomography.

Figure 2C:
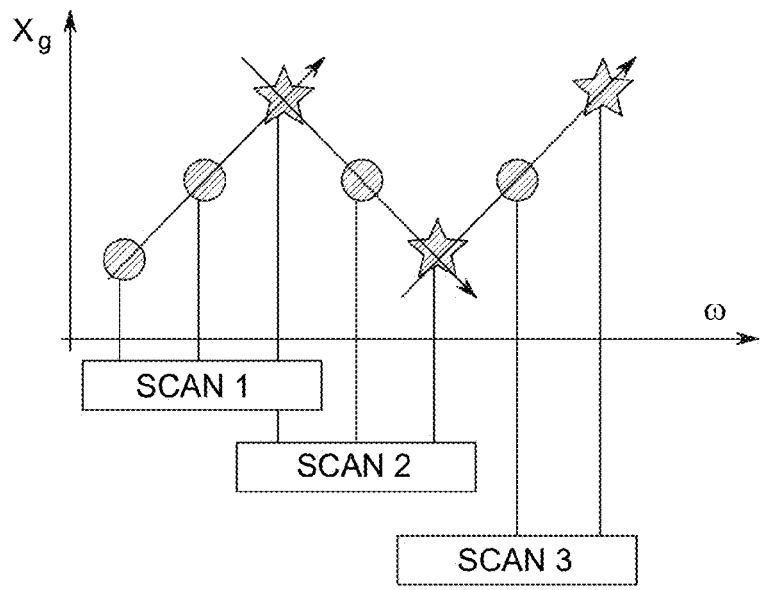
Figure 2D:
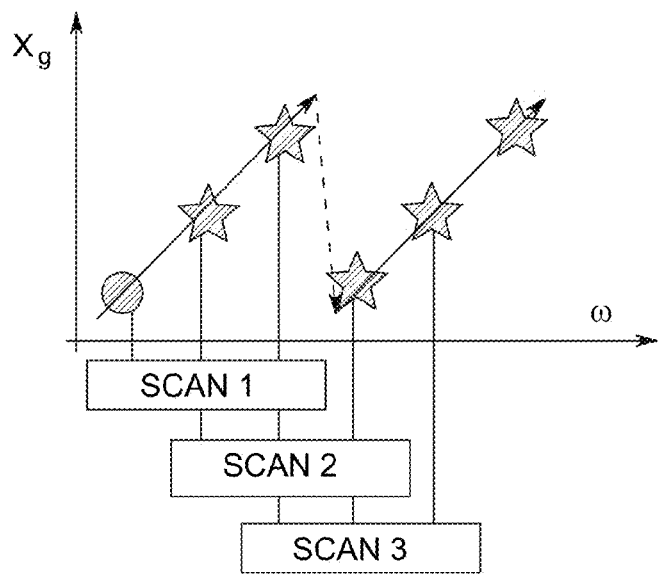

FIGS. 2C-2D depict conventional sliding window scan patterns—zigzag (FIG. 2C) and interlaced (FIG. 2D). The sliding window technique uses phase steps from neighboring views to synthesize data for all views, which again can be considered nearest-neighbor interpolation to preprocess the acquired data for conventional image reconstruction. In the sliding window zigzag technique, the first and Pth phase step are used for two views; in the sliding window interlaced technique, all phase steps are used for P views.

Figure 3:
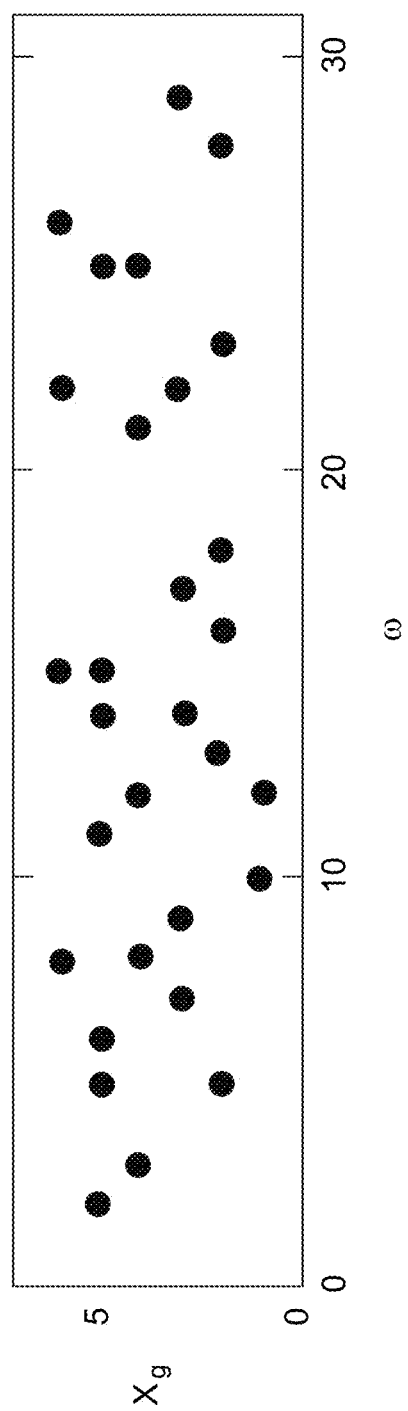
FIG. 3 depicts a random under-sampling scheme in accordance with embodiments.

FIG. 3 depicts a random under-sampling scheme in accordance with embodiments. Systematic approaches are not practical anymore because of the randomness. This randomness also does not guarantee an upper limit for the nearest neighbor error anymore. Embodying systems and methods combines phase contrast CT with the concept of compressed sensing to exploit prior knowledge about the scan subject, e.g., that its representation in specific transform domains is sparse. The compressed sensing can obtain higher under-sampling factors, and reduce scan time. Reduced scan time is commensurate with reduced patient dosage.

In accordance with embodiments, compressed sensing denotes the application of regularized reconstruction to enable image reconstruction from randomly under-sampled data. The randomness of the under-sampled data set ensures that artifacts caused by the under-sampling appear as noise in the reconstructed image. In more conventional data acquisition techniques with systematic under-sampling as described above, the artifacts due to under-sampling appear as coherent structures. Embodying systems and methods can improve the regularized reconstruction and allow for greater under-sampling factors than conventional scan schemes.

Figure 4:
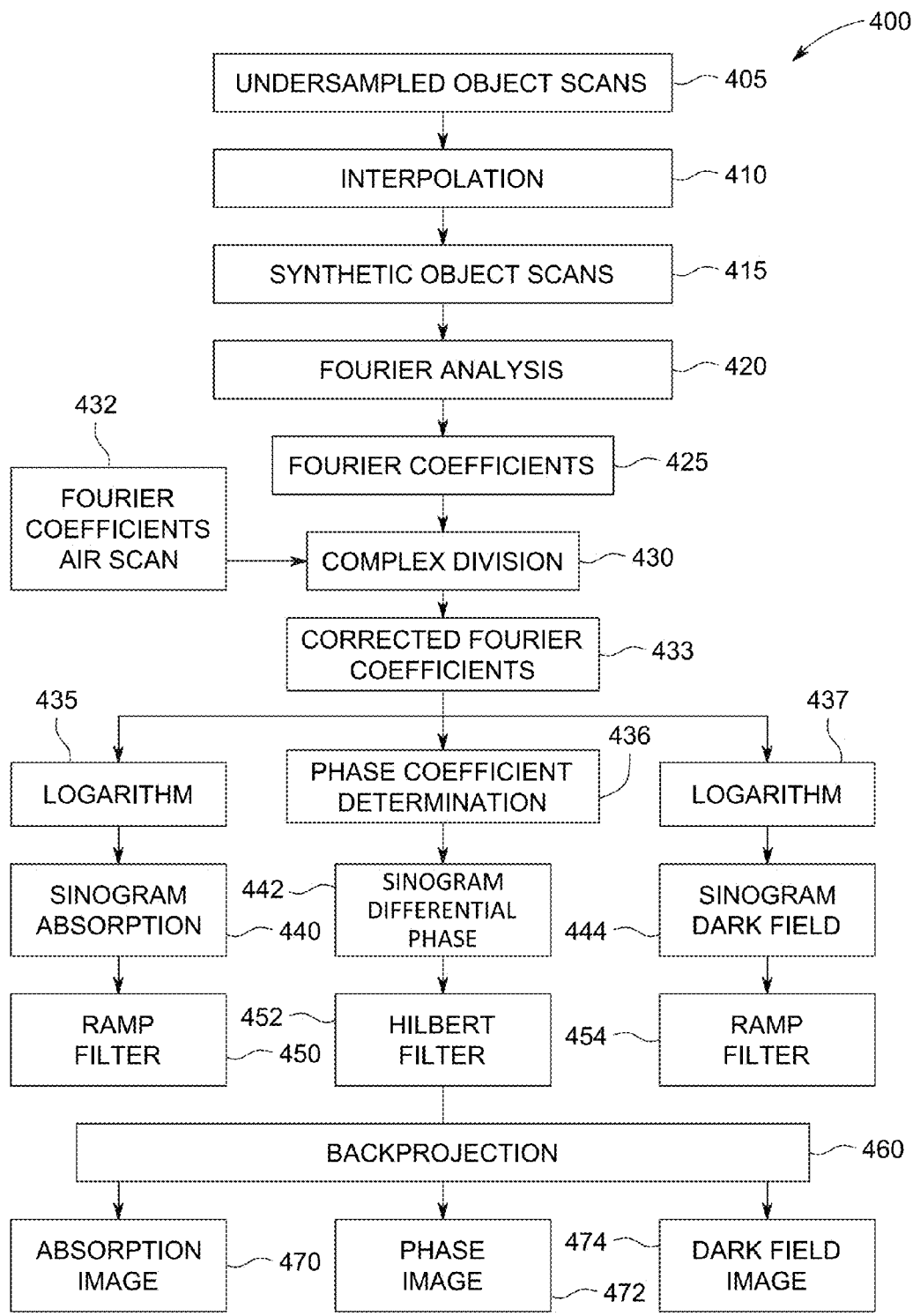
FIG. 4 depicts a conventional process for reconstruction of under-sampled PCT in accordance with embodiments.

FIG. 4 depicts conventional reconstruction process 400 of under-sampled PCT (uPCT) data. At step 405, an under-sampled object scan of the test subject is performed. In contrast to conventional techniques for PCT, a nearest neighbor interpolation is introduced, step 410, to synthesize data points between the sampled locations. A synthetic, fully-sampled object scan is created, step 415, by combining the under-sampled data points and the interpolated points.

Fourier analysis is performed in the phase stepping dimension of the data, step 420, to compute Fourier coefficients of the data, step 425. The three types of contrast provided by the PCT are an absorption image, a differential phase image, and a dark field image. Data for these three images can be computed by a complex division, step 430, of the Fourier coefficients of the object scan by the Fourier coefficients an air scan, which are obtained, step 432, to correct for system non-homogeneities to create a reference of system contributions. Using the corrected Fourier coefficients, item 433, the absorption image, differential phase image, and dark field image can be obtained.

Absorption sinogram 440 can be obtained by calculating, step 435, the logarithm of the magnitude of the $0^{th}$-order coefficient. Differential phase sinogram 442 can be obtained by determining, step 436, the phase of the $1^{st}$-order coefficient. Dark field sinogram 444 can be obtained by calculating, step 437, the logarithm of the ratio of the magnitude of $1^{st}$- and $0^{th}$-order coefficients.

The Fourier coefficients provide a different, but equivalent, description of the measurement data. This Fourier description enables to disentangle the contributions of absorption, refraction and small angle scattering to the acquired data. These Fourier coefficients do not directly describe the scan subject. Inverse Fourier analysis on these coefficients yields the measurement data back not (any of the) scan subject images.

Three different reconstructions can be performed, but each reconstruction in itself is fairly standard, with the exception of the Hilbert-like filter, instead of the ramp-like filter for the phase reconstruction. The reconstruction described is (theoretical 2D) filtered backprojection, but other options exist as well.

Filtering is performed on the individual image type sinograms; a ramp filter, step 450, is applied to the absorption sinogram; a Hilbert filter, step 452, is applied to the sinogram differential phase; and a ramp filter is applied to the dark field sinogram, step 454. Phase reconstruction requires a different filter because of the differential nature of the input data of the algorithm. A filtered backprojection, step 460, is performed to obtain analytical reconstruction images on the absorption data (step 470), phase data (step 472), and dark filed data (step 474).

Figure 5:
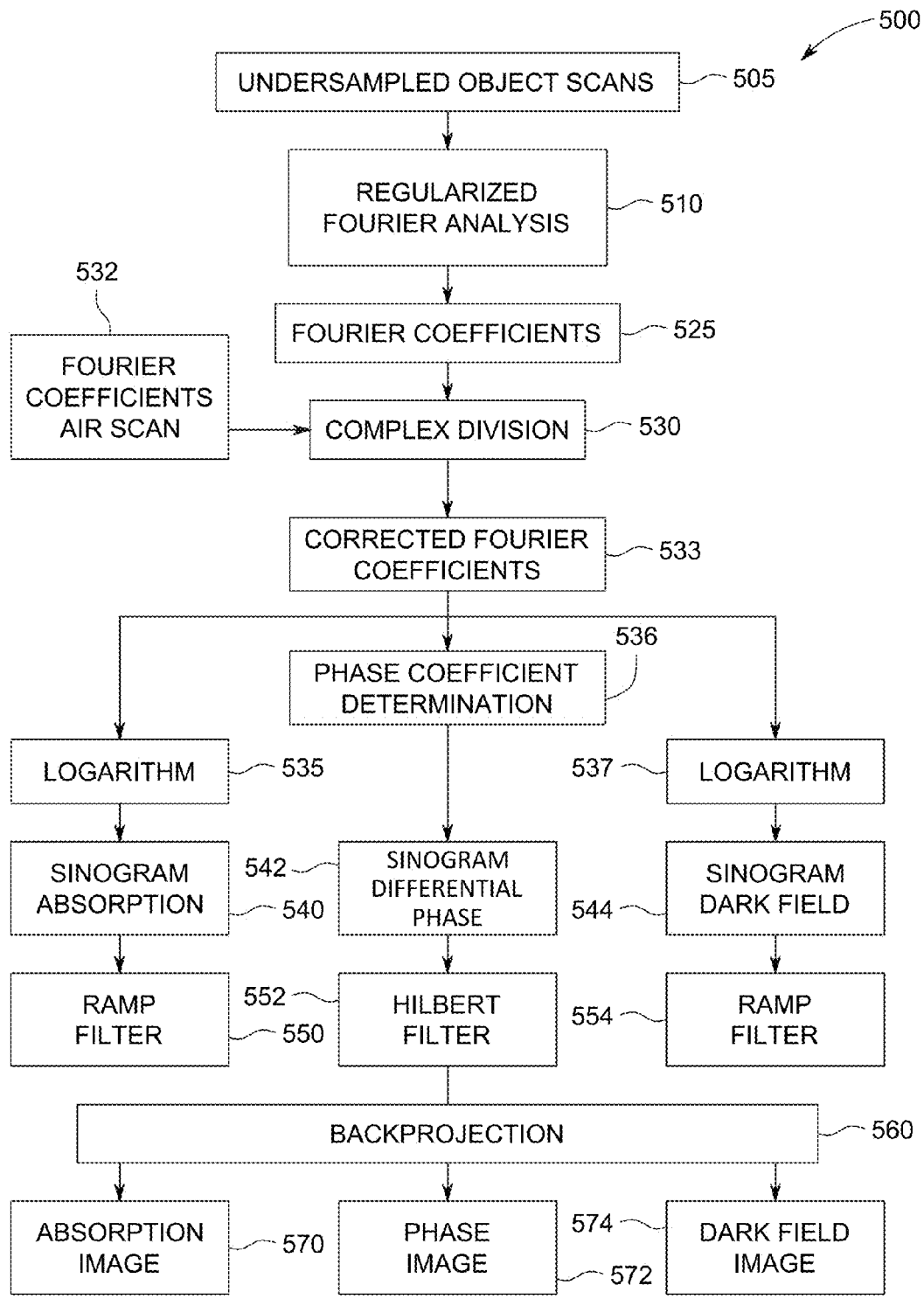
FIG. 5 depicts a process for reconstruction of under-sampled PCT in accordance with embodiments.

FIG. 5 depicts reconstruction process 500 of uPCT data in accordance with embodiments. At step 505, an under-sampled object scan of the test subject is performed. As disclosed above, the under-sampling data collection is done in a randomized manner (FIG. 3). In accordance with embodiments, the prior art interpolation (step 410) and Fourier analysis (steps 415-420) are replaced by a regularized Fourier analysis, step 510. This regularized Fourier analysis explicitly models the under-sampling by a mask operator M—i.e., by solving the minimization task of Equation 1:

$$\min_{a}\|M\mathcal{F}^{H}a - d\| + R(a) \qquad (EQ.\ 1)$$

Where:
a=the Fourier coefficients to be reconstructed;
F=the Fourier analysis matrix;
d=the measured (under-sampled) data; and
R=a regularization function.

An embodying system can include a regularizer unit configured to convert the reconstruction task from a local (pixel-by-pixel) to a global task, i.e., to exploit prior knowledge from measured or synthetic data of the other (typically neighboring) detector pixels (x,y) and/or measured or synthetic data from other (typically neighboring) view angles (ω), or even from the fact that tomographic data is acquired, i.e. from a (filtered) backprojection of (parts of) the Fourier coefficients 'a'. This reconstruction can be applied on either one of the Fourier coefficients (typically $0^{th}$ or $1^{st}$ order coefficients are computed), or to both. For local pixel-by-pixel regularization, the Fourier coefficients 'a' and measured data 'd' in EQ. 1 are interpreted as vectors with as many vector elements as there are (measured or synthetic) phase steps.

The matrices 'M' and '$F^H$' and the regularization function 'R' are interpreted accordingly. As a result there are as many vectors 'a' and 'd', and therefore also as many equations EQ. 1, as there are detector pixels times view angles. The optimization in EQ. 1 can thereby be performed on a per detector pixel and view angle basis. For the global task, the Fourier coefficients 'a' and measured data 'd' in EQ. 1 are interpreted as vectors with as many vector elements as there are (measured or synthetic) phase steps times detector pixels times view angles.

The matrices 'M' and '$F^H$' and the regularization function 'R' are again interpreted accordingly and are different from 'M', '$F^H$' and 'R' for the local regularization task. As a result there is only a single equation EQ. 1 to be optimized, but the regularization function 'R' is defined in a much higher dimensional space enabling it to perform more sophisticated regularization.

It should readily be understood that "intermediate" versions between the above local and general global regularization tasks are equally possible. Further, it should also clear that the above general global regularization also comprises regularization functions 'R' that perform regularization based on (partially) reconstructed images of the absorption, phase and/or dark field obtained from linear reconstruction algorithms, like filtered backprojection. In some implementations, embodying systems and methods can perform non-linear image reconstruction, and then use that reconstruction in the regularization. Typical choices of the regularization function 'R' would be minimum Total Variation, wavelet sparsity, sparse representation in (learned) dictionary. Also several regularizers could be combined. For example, different regularizer units, say R1 and R2, are combined to yield min_a|| . . . ||+R1(a)+R2(a).

Having performed a regularized Fourier analysis (step 510) in place of the conventional interpolation and Fourier analysis (steps 410, 415, 420), the remaining steps of process 500 (steps 525-574) to obtain analytical reconstruction images of the absorption data, phase data, and dark field data are similar in nature as the correspondingly-numbered claims of process 400 (steps 425-474).

Fourier coefficients of the data, step 525, is computed. A complex division, step 530, of the Fourier coefficients of the object scan by the Fourier coefficients of an air scan, which are obtained, step 532, to correct for system non-homogeneities create a reference of system contributions.

Using the corrected Fourier coefficients, item 533, data for an absorption image, a differential phase image, and a dark field image can be computed. Absorption sinogram 540 can be obtained by calculating, step 535, the logarithm of the magnitude of the $0^{th}$-order coefficient. Differential phase sinogram 542 can be obtained by determining, step 536, the phase of the $1^{st}$-order coefficient. Dark field sinogram 544 can be obtained by calculating, step 537, the logarithm of the ratio of the magnitude of $1^{st}$- and $0^{th}$-order coefficients. Filtering is performed on the individual image type sinograms; a ramp filter, step 550, is applied to the absorption sinogram; a Hilbert filter, step 552, is applied to the sinogram differential phase; and a ramp filter is applied to the dark field sinogram, step 554. A filtered backprojection, step 560, is performed to obtain analytical reconstruction images on the absorption data (step 570), phase data (step 572), and dark filed data (step 574).

Figure 6:
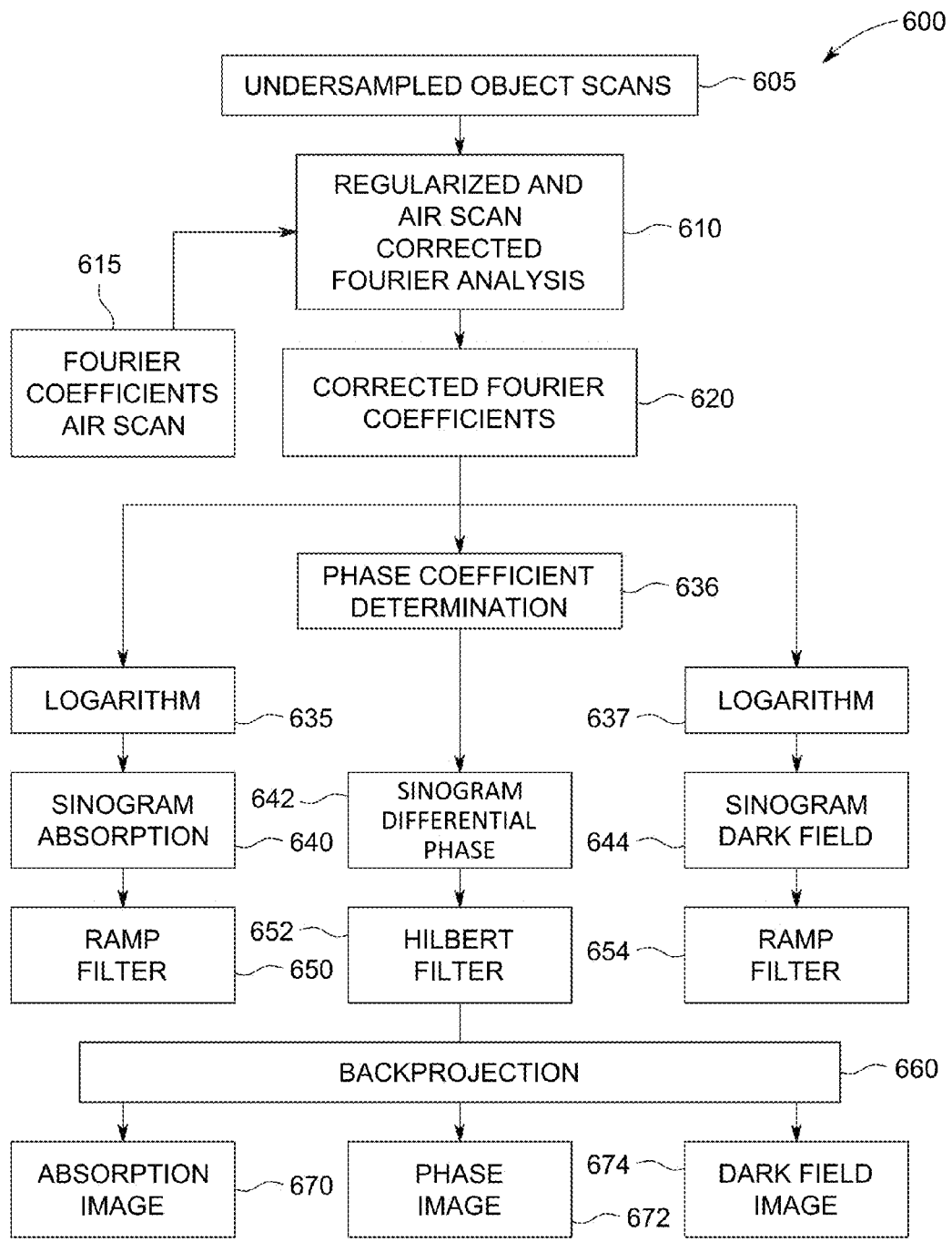
FIG. 6 depicts another process for reconstruction of under-sampled PCT in accordance with embodiments.

FIG. 6 depicts reconstruction process 600 of PCT or uPCT data in accordance with embodiments. At step 605, an under-sampled object scan of the test subject is performed.

As disclosed above, the under-sampling data collection is done in a randomized manner (FIG. 3). In accordance with embodiments, the prior art interpolation (step 410) and Fourier analysis (steps 415-420) are replaced by a regularized Fourier analysis, step 610, that includes correction for the system inhomogeneity derived from the air scan data 615. In accordance with implementations, this regularized Fourier analysis includes the division by the Fourier object scan coefficients of the Fourier coefficients of an air scan, step 615.

Such a regularized Fourier analysis incorporating system corrections can be achieved by solving the minimization task of Equation 2 to obtain corrected Fourier coefficients (step 620):

$$\min_b \|M\mathcal{F}^H Cb - d\| + R(b) \qquad (EQ.\ 2)$$

Where:
b=Fourier coefficients to be reconstructed after correction for the system inhomogeneity;
C=an operator that "uncorrects" the Fourier coefficients to match the measured, under-sampled (uncorrected) data d; and
R=a regularization function.

Having performed a regularized Fourier analysis (step 610)—in place of the conventional interpolation and Fourier analysis (steps 410, 415, 420), which also incorporates both the complex division (step 430) and the system correction (step 432), the remaining steps of process 600 (steps 635-674) to obtain analytical reconstruction images of the absorption data, phase data, and dark field data are similar in nature as the correspondingly-numbered claims of process 400 (steps 435-474).

Using the corrected Fourier coefficients, item 620, data for an absorption image, a differential phase image, and a dark field image can be computed. Absorption sinogram 640 can be obtained by calculating, step 635, the logarithm of the magnitude of the $0^{th}$-order coefficient. Differential phase sinogram 642 can be obtained by determining, step 636, the phase of the $1^{st}$-order coefficient. Dark field sinogram 644 can be obtained by calculating, step 637, the logarithm of the ratio of the magnitude of $1^{st}$- and $0^{th}$-order coefficients.

Filtering is performed on the individual image type sinograms; a ramp filter, step 650, is applied to the absorption sinogram; a Hilbert filter, step 652, is applied to the sinogram differential phase; and a ramp filter is applied to the dark field sinogram, step 654. A filtered backprojection, step 660, is performed to obtain analytical reconstruction images on the absorption data (step 670), phase data (step 672), and dark filed data (step 674).

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method to regularize the reconstruction of randomly under-sampled imaging data to improve the image quality based on prior knowledge by implementing compressed sensing, as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

The invention claimed is:

1. A method for reconstructing under-sampled phase contrast computed tomography data, the method comprising:
    obtaining under-sampled scan data of a subject-under-test, the object scan performed on a phase contrast computed tomography (PCT) system;
    performing a regularized Fourier analysis on the under-sampled scan data;
    correcting for one or more PCT system contributions to the under-sampled scan data by dividing the computed Fourier coefficients by Fourier coefficients representative of the one or more PCT system contributions;
    obtaining at least one of an absorption sinogram, a differential phase sinogram, and a dark field sinogram from the corrected Fourier coefficients; and
    performing tomographic reconstruction on the obtained absorption sinogram, the obtained differential phase sinogram, and the obtained dark field sinogram.

2. The method of claim 1, including collecting the under-sampled object scan data in a randomized manner.

3. The method of claim 1, including obtaining the Fourier coefficients representative of the one or more PCT system contributions by performing an air scan.

4. The method of claim 1, wherein the dividing step corrects the computed Fourier coefficients for PCT system non-homogeneities.

5. The method of claim 1, the regularized Fourier analysis step including solving a minimization equation expressed as $$\min_{a} \|M\mathcal{F}^H a - d\| + R(a).$$

6. The method of claim 1, wherein the regularized Fourier analysis step includes the correcting step.

7. The method of claim 6, including the regularized Fourier analysis step including solving a minimization equation expressed as $$\min_{b} \|M\mathcal{F}^H Cb - d\| + R(b).$$

8. A non-transitory computer-readable medium having stored thereon instructions which when executed by a processor cause the processor to perform a method for reconstructing under-sampled phase contrast computed tomography data, the method comprising:
    obtaining under-sampled scan data of a subject-under-test, the object scan performed on a phase contrast computed tomography (PCT) system;
    performing a regularized Fourier analysis on the under-sampled scan data;
    computing Fourier coefficients for the under-sampled scan data;
    correcting for one or more PCT system contributions to the under-sampled scan data by dividing the computed Fourier coefficients by Fourier coefficients representative of the one or more PCT system contributions;
    obtaining at least one of an absorption sinogram, a differential phase sinogram, and a dark field sinogram from the corrected Fourier coefficients; and
    performing tomographic reconstruction on the obtained absorption sinogram, the obtained differential phase sinogram, and the obtained dark field sinogram.

9. The non-transitory computer-readable medium of claim 8, including instructions to cause the processor to collect the under-sampled object scan data in a randomized manner.

10. The non-transitory computer-readable medium of claim 8, including instructions to cause the processor to obtain the Fourier coefficients representative of the one or more PCT system contributions by performing an air scan.

11. The non-transitory computer-readable medium of claim 8, including instructions to cause the processor to correct the computed Fourier coefficients for PCT system non-homogeneities during the dividing step.

12. The non-transitory computer-readable medium of claim 8, including instructions to cause the processor to perform the regularized Fourier analysis step by solving a minimization equation expressed as $$\min_{a} \|M\mathcal{F}^H a - d\| + R(a).$$

13. The non-transitory computer-readable medium of claim 8, including instructions to cause the processor to combine the regularized Fourier analysis step and the correcting step.

14. The non-transitory computer-readable medium of claim 13, including instructions to cause the processor to perform the regularized Fourier analysis step by solving a minimization equation expressed as $$\min_{b} \|M\mathcal{F}^H Cb - d\| + R(b).$$

15. A phase contrast computed tomography (PCT) system comprising:
    an x-ray emitting tube positioned to emit x-rays towards a scan subject;
    a phase/absorption grating window on a side of the scan subject distal from the x-ray emitting tube;
    an absorption window distal from the phase/absorption window;
    an x-ray detector distal from the absorption window;
    a control processor configured to execute computer instructions to cause the processor to perform a method for reconstructing under-sampled phase contrast computed tomography data, the method including:

obtaining under-sampled scan data of a subject-under-test, the object scan performed on a phase contrast computed tomography (PCT) system;

performing a regularized Fourier analysis on the under-sampled scan data;

computing Fourier coefficients for the under-sampled scan data;

correcting for one or more PCT system contributions to the under-sampled scan data by dividing the computed Fourier coefficients by Fourier coefficients representative of the one or more PCT system contributions;

obtaining at least one of an absorption sinogram, a differential phase sinogram, and a dark field sinogram from the corrected Fourier coefficients; and performing tomographic reconstruction on the obtained absorption sinogram, the obtained differential phase sinogram, and the obtained dark field sinogram.

16. The system of claim 15, including a regularizer unit configured to convert the reconstruction method from a local pixel-by-pixel task to a global task by exploiting prior knowledge from measured or synthetic data of at least one of neighboring detector pixels, and measured or synthetic data from neighboring view angles.

17. The system of claim 15, including computer instructions to cause the control processor to collect the under-sampled object scan data in a randomized manner.

18. The system of claim 15, including instructions to cause the control processor to perform the regularized Fourier analysis step by solving a minimization equation expressed as $$\min_a \|M\mathcal{F}^H a - d\| + R(a).$$

19. The system of claim 15, including instructions to cause the processor to combine the regularized Fourier analysis step and the correcting step.

20. The system of claim 19, including instructions to cause the control processor to perform the regularized Fourier analysis step by solving a minimization equation expressed as $$\min_b \|M\mathcal{F}^H Cb - d\| + R(b).$$

* * * * *